United States Patent
Lowkis et al.

(10) Patent No.: US 11,844,749 B2
(45) Date of Patent: Dec. 19, 2023

(54) ENTERAL FLUID DELIVERY SYSTEM

(71) Applicant: Medline Industries, LP, Northfield, IL (US)

(72) Inventors: Paulina Lowkis, Barrington, IL (US); Michael Turturro, Arlington Heights, IL (US); Luke Stevens, Long Grove, IL (US); Lisa Bauer, Buffalo Grove, IL (US); Morgan Uridil, Evanston, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 17/734,475

(22) Filed: May 2, 2022

(65) Prior Publication Data

US 2022/0249329 A1    Aug. 11, 2022

Related U.S. Application Data

(62) Division of application No. 16/522,814, filed on Jul. 26, 2019, now Pat. No. 11,344,480.

(60) Provisional application No. 62/703,561, filed on Jul. 26, 2018.

(51) Int. Cl.
*A61J 15/00* (2006.01)
*A61M 5/14* (2006.01)

(52) U.S. Cl.
CPC ....... *A61J 15/0015* (2013.01); *A61J 15/0003* (2013.01); *A61J 15/0026* (2013.01); *A61M 5/1411* (2013.01); *A61J 15/0011* (2013.01)

(58) Field of Classification Search
CPC .......................... A61J 15/0026; A61J 15/0011; A61J 15/0096; A61J 15/0015; A61J 1/05; A61J 1/03; A61J 1/14; A61M 5/1411; A61M 2205/7536; A61M 39/00
See application file for complete search history.

(56) References Cited

U.S. PATENT DOCUMENTS

| | | | | |
|---|---|---|---|---|
| 4,271,973 | A * | 6/1981 | Quagliaro | B65D 51/1616 215/261 |
| 6,012,596 | A * | 1/2000 | Oglesbee | A61J 1/1487 141/330 |
| 2011/0118676 | A1* | 5/2011 | Kropczynski, Jr. | A61M 5/162 604/257 |
| 2016/0220798 | A1* | 8/2016 | Netzel | A61M 5/14244 |
| 2019/0151200 | A1* | 5/2019 | McDowell | A61J 1/1431 |

* cited by examiner

*Primary Examiner* — James D Ponton
*Assistant Examiner* — Neeraja Gollamudi
(74) *Attorney, Agent, or Firm* — Fitch, Even, Tabin & Flannery LLP

(57) ABSTRACT

Disclosed is a system for administrating fluids to a patient, such as an infant. The system comprises a container that defines a drip chamber, a source of nutritive fluid fluidically communicating with the drip chamber, and a tube connecting the drip chamber to the gastric cavity of a patient, the chamber including a membrane that is gas-permeable but that is resistant to fluid passage. The system allows fluids to be introduced to the patient and for gastric gases to be released while they are resistant to the leak and spillage.

14 Claims, 16 Drawing Sheets

ENTERAL FLUID DELIVERY SYSTEM

CROSS-REFERENCE TO RELATED APPLICATIONS

This application is a divisional of U.S. application Ser. No. 16/522,814 filed Jul. 26, 2019, which claims the benefit of U.S. Provisional Application No. 62/703,561, filed Jul. 26, 2018, which are hereby incorporated by reference as if fully set forth herein.

This application is related to U.S. application Ser. No. 16/256,414, entitled "Feeding Syringe Holder" and filed Jan. 24, 2019, which is hereby incorporated by reference as if fully set forth herein.

FIELD

This disclosure is in the field of delivery of liquid nutrients to a patient by a caregiver, such as in a hospital setting.

BACKGROUND

When a patient is unable to eat normally, it is necessary to provide nutrition to the patient in other ways. It is known to provide nutrition via enteral feeding tubes by which a tube is placed into the gastric cavity of the patient and nutritive fluids are introduced to the patient through this tube. The nutritive fluids may be fed via gravity or via mechanical pumping to the patient. Often, a barrel syringe is used to provide a drip chamber whereby the tip of the syringe is connected to the feeding tube and fluid is introduced to the syringe. Particularly in the case of infants, gastric gases are released by the patient. If the patient is unable to release gastric gases on his or her own, gastric gases can travel back through the feeding tube and be introduced to the syringe, causing potential spilling, leaks, blockages, or overflows.

Now, a new feeding system has been devised, the feeding system including a container defining a drip chamber connected at one end to a feeding tube that is positioned for placement within the gastric cavity of the patient for enteral feeding. The drip chamber is fluidically connected to a source of nutritive fluid, which is typically caused to be introduced into the chamber via a pump or via gravity feeding. The container is provided with a gas-permeable membrane that is resistant to liquid spillage, typically a hydrophobic membrane. A hanging hook may be provided to elevate the container relative to the patient to enable gravity feeding of nutritive fluid through the patient. Because the membrane is gas-permeable but resistant to liquid leakage, the attendant problems of leakage and spilling of formula may be mitigated.

DETAILED DESCRIPTION

Figure 1:
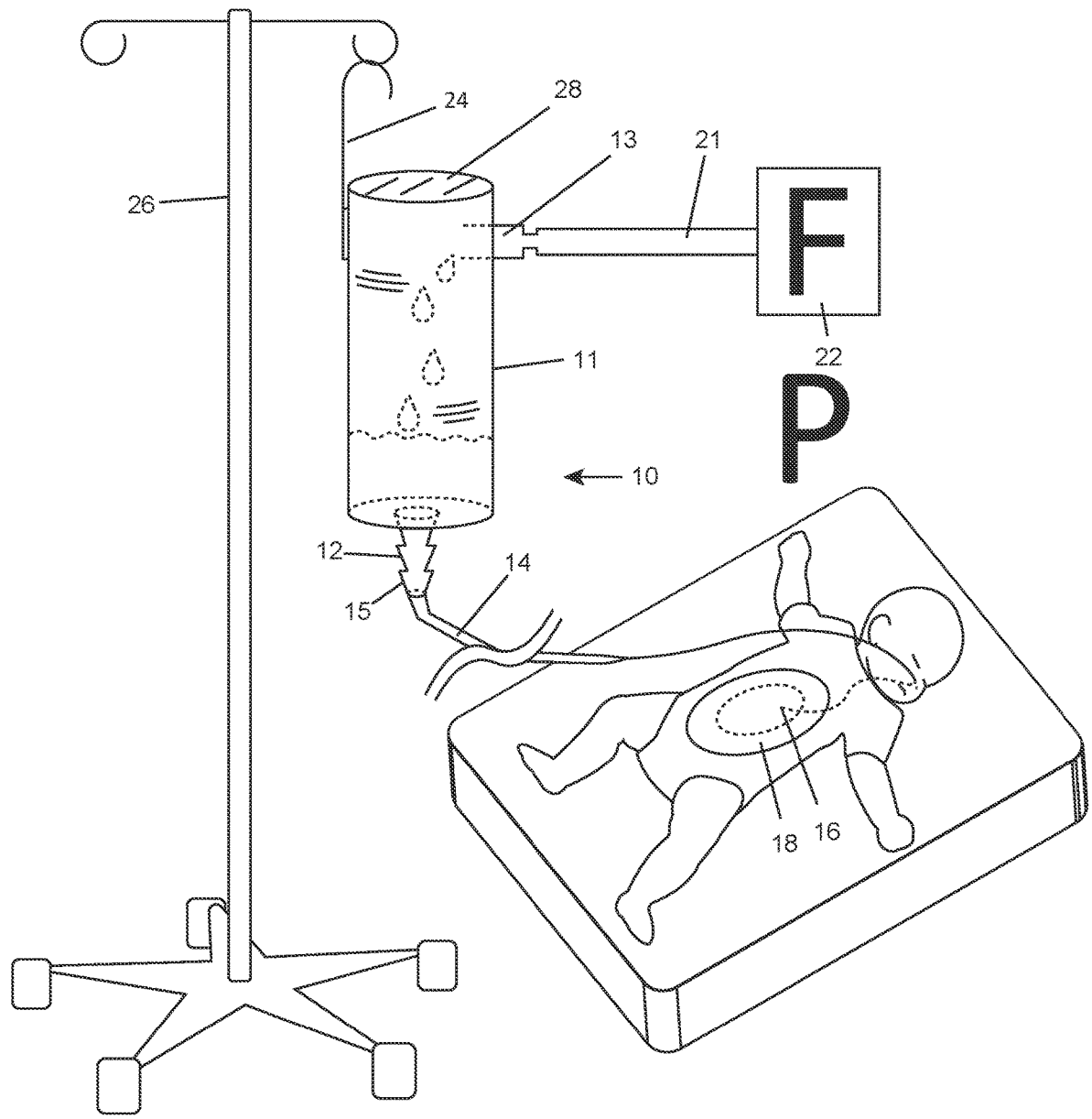
FIG. 1 is a representational view of a feeding system in accordance with one embodiment in the invention and being used to deliver nutritive fluid to a patient.
Figure 2:
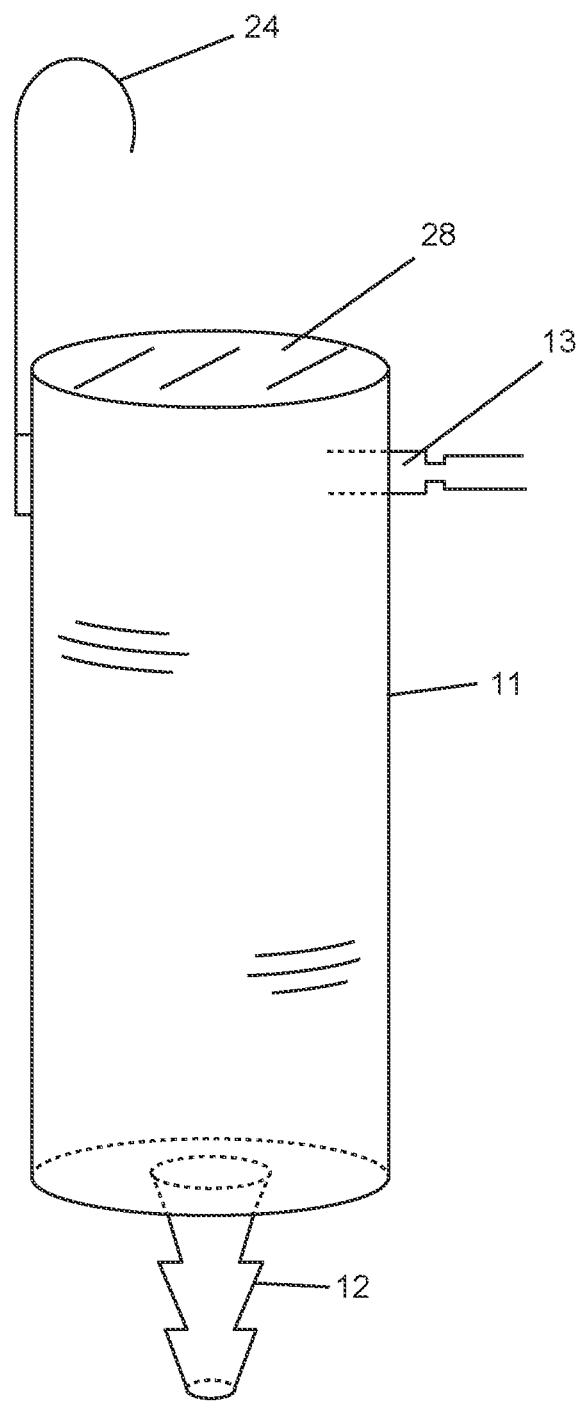
FIG. 2 is a relatively enlarged perspective view of the syringe container used in feeding system shown in FIG. 1.

With reference to FIG. 1, the system 10 includes a barrel syringe 11 that defines a container, the syringe including plural ports. These include a first port 12 and a second port 13. The first port 12 is connected to gastric tubing 14 at a first end 15 of the tubing, the second end 16 of the tubing being introduced to the gastric cavity of a patient 18 for enteral feeding. The second port 13 fluidically communicates through a conduit 21 to a source 22 of nutritive fluid. In one approach, one or both of the first and second ports 12, 13 can include a one-way valve disposed to prevent backflow of material. During use, for example, such a one-way valve can prevent a backflow of the consumer's digestive fluids and solids, gases, and so forth. Various known one-way valves can be so employed as desired.

The gastric tubing 14 may be a flexible material such as, but not limited to, silicon. "Feeding tubes" are known in the art and constitute a flexible tube (often comprised of silicon) that is designed, packaged, and distributed for exclusive use in enteral feeding by having one end of the tube placed directly within the consumer's digestive tract (i.e., the stomach or the small intestine) via that person's nose or mouth (by one approach) or via an opening formed in and through the user's skin (by another approach).

A pump (shown generally at P) may be used to force fluid through the conduit 21 into the container 11, or the liquid nutritive material may be introduced via gravity feeding. The syringe 11 is provided with a hook 24 which hangs on a conventional hanger pole 26, the hook being positioned in an elevated location relative to the patient to allow for gravity feeding. In operation, the pump is activated or the fluid is introduced through the conduit via gravity into the container, whereby fluid drips into the container and is introduced in a controlled rate through the gastric tube into the gastric cavity of the patient.

As illustrated, the barrel syringe includes a membrane 28 disposed at a top opening thereof. In this way, the membrane 28 may be disposed gravitationally above the port 13 when the syringe 11 receives fluid. The membrane may be any suitable gas-permeable membrane that is resistant to passage of liquids, and thus, for example, hydrophobic membranes such as polyurethane may be employed.

The membrane 28 may be a liquid impermeable and breathable fabric that resists liquid material water passing through, but allows gases to pass through. "Breathable" when used in describing a membrane means that the membrane has the ability to allow moisture vapor to be transmitted through the material. Breathable membranes may be air permeable, but it is not necessary to be air permeable to be breathable. "Liquid impermeable," when used in describing a membrane means that liquid will not pass through the membrane, under ordinary use conditions, in a direction generally perpendicular to the plane of the membrane at the point of liquid contact.

The membrane 28 may have a moisture vapor transmission rate value (MVTR) (also called water vapor transmission rate (WVTR)), of greater than approximately 300 g/m²/day (e.g., as described by ASTM E96—Water Vapor Transmission of Materials Using Gravimetric Method). In some approaches, the membrane has a MVTR in the range of about 1000 g/m²/day to about 10,000 g/m²/day. For example, the third layer may have a MVTR of about 1000 g/m²/day, about 2000 g/m²/day, about 3,000 g/m²/day, about 4000 g/m²/day, about 5000 g/m²/day, approximately 6,000 g/m²/day, about 7000 g/m²/day, about 8000 g/m²/day, about 9000 g/m²/day, about 10000 g/m²/day, or about 20000 g/m²/day, including all ranges and subranges located between themselves.

For example, the MTRV may be in the range of approximately 5,000 g/m²/day to approximately 20,000 g/m²/day (e.g., as measured by the Japanese Industry Standards L 1099 testing methods for water vapor permeability of textiles).

In one example, the membrane 28 is formed of polytetrafluoroethylene (PTFE) that is laminated to a non-woven polyester support material. "Non-woven" refers to materials and webs of material that are formed without the aid of a textile weaving or knitting process. For example, nonwoven materials, fabrics or webs have been formed from many processes such as meltblowing processes, spunbonding processes, air laying processes, and bonded carded web processes. The membrane can then be sealed using ultrasonic welding, RF welding, and adhesive to name a few. The membrane (e.g., the PTFE layer) may have pores having pore sizes of approximately, for example, 0.02 μm, 0.2 μm, 0.45 μm, or 1 μm. The membrane may have an average thickness, for example, in the range of 139.7-279.4 μm, 203.2-330.2 μm, 198.1-269.2 μm, or 177.8-279.4 μm. The membrane may have an average water breakthrough of >20.0 psi, >30 psi, >80 psi, or >230 psi. The membrane may have an average Gurley airflow (sec/100 cc/20 oz/1.0 int) of <75.0, 9.0-23., 4.0-17.0, or <11.1.

In still another example, the membrane is a hydrophilic nylon membrane. The membrane may have a pore size of approximately, for example, 0.2 μm, 0.45 μm, 0.8 μm, or 1.2 μm.

In still another aspect, the membrane 28 may include one or more natural or synthetic fabrics that are laminated to or coated with a waterproofing material such as rubber, polyvinyl chloride (PVC), polyurethane (PU), silicone elastomer, fluoropolymers, and wax.

In still another aspect, the membrane 28 is manufactured from a thermoplastic polyethylene film (TPE) or a thermoplastic polyurethane (TPU) that is configured to be breathable via the inclusion of micropores that allow vapor to penetrate the TPU or TPE while precluding liquids from passing through the same. Breathable TPU or TPE is well suited as the membrane 28 due to its high durability, high abrasion resistance, and low-temperature flexibility.

As such, the membranes described herein may be composed of a moisture-pervious fabric suitable to allow discharge to pass therethrough. Non-limiting examples of materials suitable to form the membrane include polypropylene, polyethylene, polyester, materials having hydrophobic properties, combinations thereof and/or the like. Additionally, the membrane can be treated with a hydrophilic finish. Non-limiting examples of suitable hydrophilic finishes include stearic acid, melamine-based chemicals, fluorocarbon chemicals, and silicon-based chemicals.

When, during the course of feeding the patient, gastric gases are generated and travel back through the gastric tube, the gases are released through the membrane. Any splashing of fluid will be resisted by the membrane, however, and if the container is placed on its side the container will be resistant to leakage.

Figure 3:
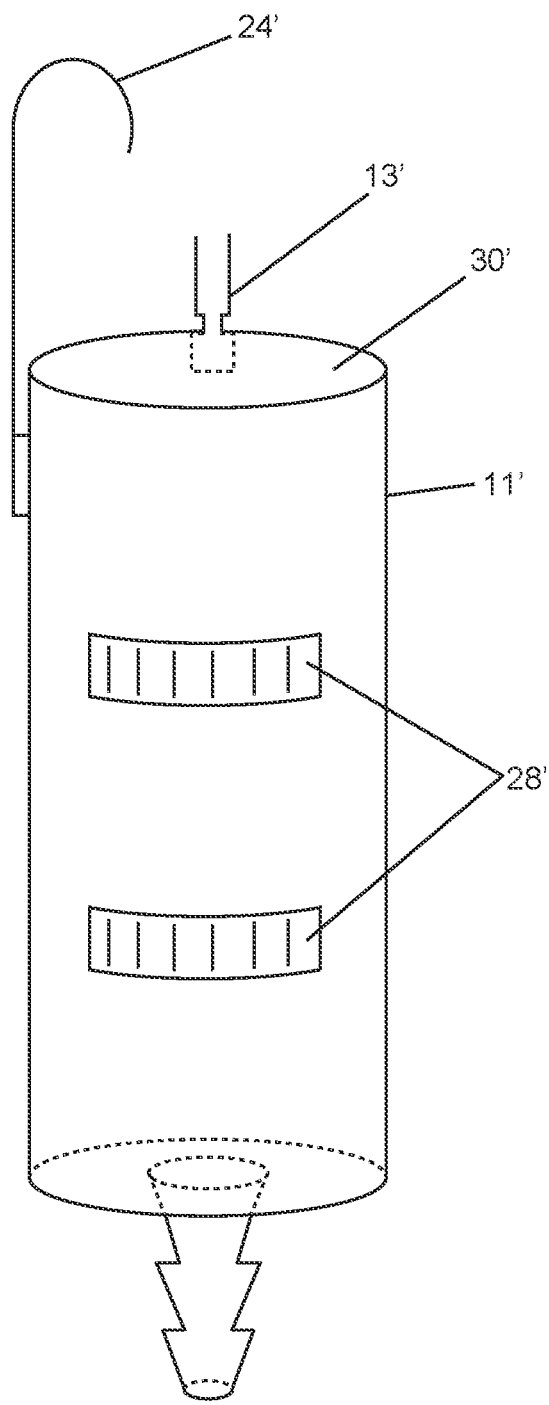
FIG. 3 is a perspective view of an alternative embodiment of the syringe container.

The positions of the port and of the membrane on the barrel syringe are not critical, and, for example, the port 13' may be placed on a cap 30' that screws onto the top of the syringe 11' as shown in FIG. 3. The syringe 11' may include membrane portions 28' disposed in a wall surface thereof. Alternatively, a hinged cap (not shown) or other cap structure may be employed. The cap structure is useful for introducing a bolus of fluid to the container, if desired. As shown, one or more of the membrane portions 28' of the syringe 11' of FIG. 3 may be disposed gravitationally below the port 13'.

Figure 4:
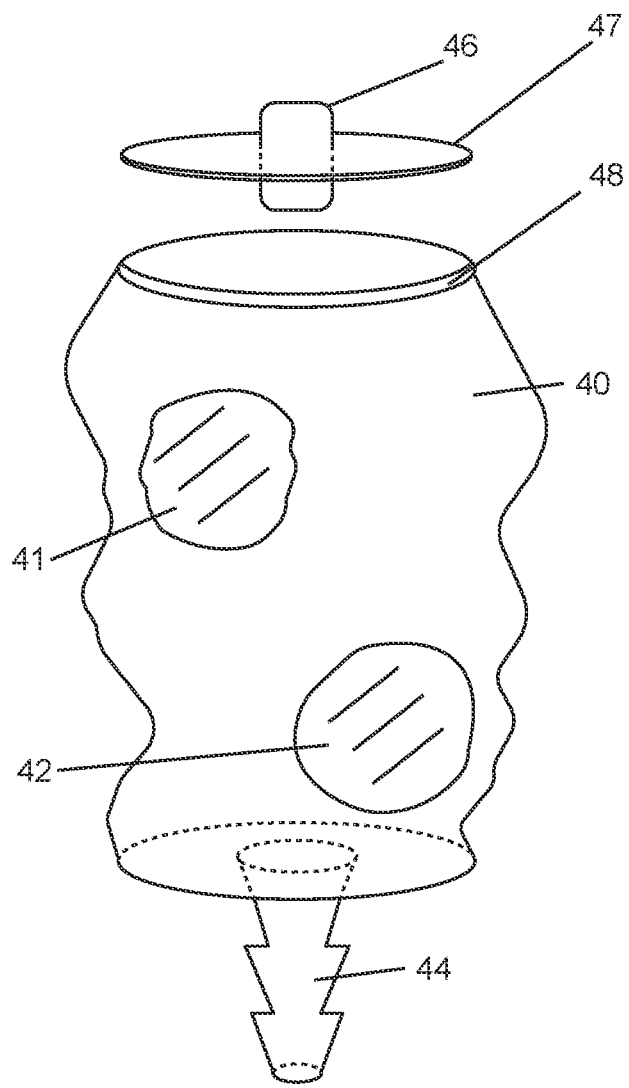
FIG. 4 is a perspective view of an alternative embodiment of a container useful in the system shown in FIG. 1.

The container need not be a barrel syringe container, but to the contrary a bagged container 40, as shown in FIG. 4 may be provided. The bagged container contains membrane structures 41, 42 covering aperture in the bagged container 40. A first port 44 is disposed at a bottom region of the container 40 and a second port 46 is disposed in a plug 47 that fits onto silicon ring structure 48, which is provided for rigidity and for cap retention purposes.

The syringe or bagged material may be composed of suitable conventional materials, such as plastics, and any suitable structure for the ports, such as luer structures, may be employed.

As such, a food nutrition system is provided. The food nutrition system includes a container defining a drip chamber that includes a gas-permeable membrane that is resistant to liquid passage therethrough. The membrane may be, or may include, a hydrophobic membrane. For example, at least a portion of the membrane may be formed of polyurethane. In one aspect, the chamber may include a rigid-wall chamber, and may include a removable cap (e.g., a screw cap). In another aspect, the container includes a non-rigid-wall structure.

A gravity fed port fluidically communicates with the drip chamber at a bottom portion thereof. A gastric tube is connected to the port at one end. The gastric tube has another end configured for placement within the gastric cavity of a patient. A fluid introduction port in the chamber fluidically communicates with a source of nutritive fluid.

In one aspect, the food nutrition system includes a hook for supporting the container. The food nutrition system may further include a pump for introducing nutritive fluid into the container.

In one approach, a food nutrition container includes a first body material that at least partially defines a drip chamber, and a membrane secured to the first body material. At least a portion of the membrane is formed of a second material that is different than the first body material. The second material is a gas-permeable, hydrophobic material. In one aspect, the membrane has a moisture vapor transmission rate value (MVTR) of greater than approximately 300 g/m²/day.

The food nutrition container may further include an inlet that is in fluidic communication with the drip chamber. The food nutrition container may further include an outlet that is disposed at a bottom portion of the food nutrition container gravitationally below the membrane. The outlet may be in fluidic communication with the drip chamber.

In one approach, the membrane is at least partially formed of polytetrafluoroethylene. In another approach, the membrane is a hydrophilic nylon membrane. In still another approach, the membrane is a synthetic fabric having a waterproofing coating. In one approach, the membrane may include a non-woven polyester support material secured to the polytetrafluoroethylene.

The membrane may include pores for permitting gaseous transmission from the drip chamber to pass through the membrane. The pores may have pore sizes in the range, for example, of approximately 0.02 µm to approximately 1 µm.

In one approach, a method is provided. The method includes providing a food nutrition container having a first body material and a membrane secured to the first body material. The first body material and the membrane at least partially define a drip chamber. At least a portion of the membrane is formed of a second material that is different than the first body material. The second material is a gas-permeable, hydrophobic material. The method further includes securing a first conduit to an inlet port of the food nutrition container. The method further includes securing a second conduit to an outlet port of the food nutrition container. The outlet port is disposed at a bottom portion of the food nutrition container gravitationally below the membrane and in fluidic communication with the drip chamber.

In one aspect of the present disclosure, a holder is provided for a syringe body of a formulated food solution delivery system. The holder includes a handle configured to be hung on a support and a body connected to the handle. The body has a central opening for receiving a barrel of a syringe body and is configured to keep the syringe body upright with the handle hung on the support. The body includes at least one alignment portion of the body configured to engage at least one protrusion of the syringe body and resist turning of the syringe body in the central opening of the body.

In another aspect of the present disclosure, a system is provided for administering a liquid food product. The system includes a syringe body having a collar, a barrel, and at least one protrusion. The system includes a handle configured to be hung on a support and a holder body connected to the handle. The holder body has a central opening sized to receive the syringe body. The holder body includes at least one alignment portion configured to engage at least one protrusion of the syringe body and resist turning of the syringe body in the central opening of the holder body.

Figure 5:
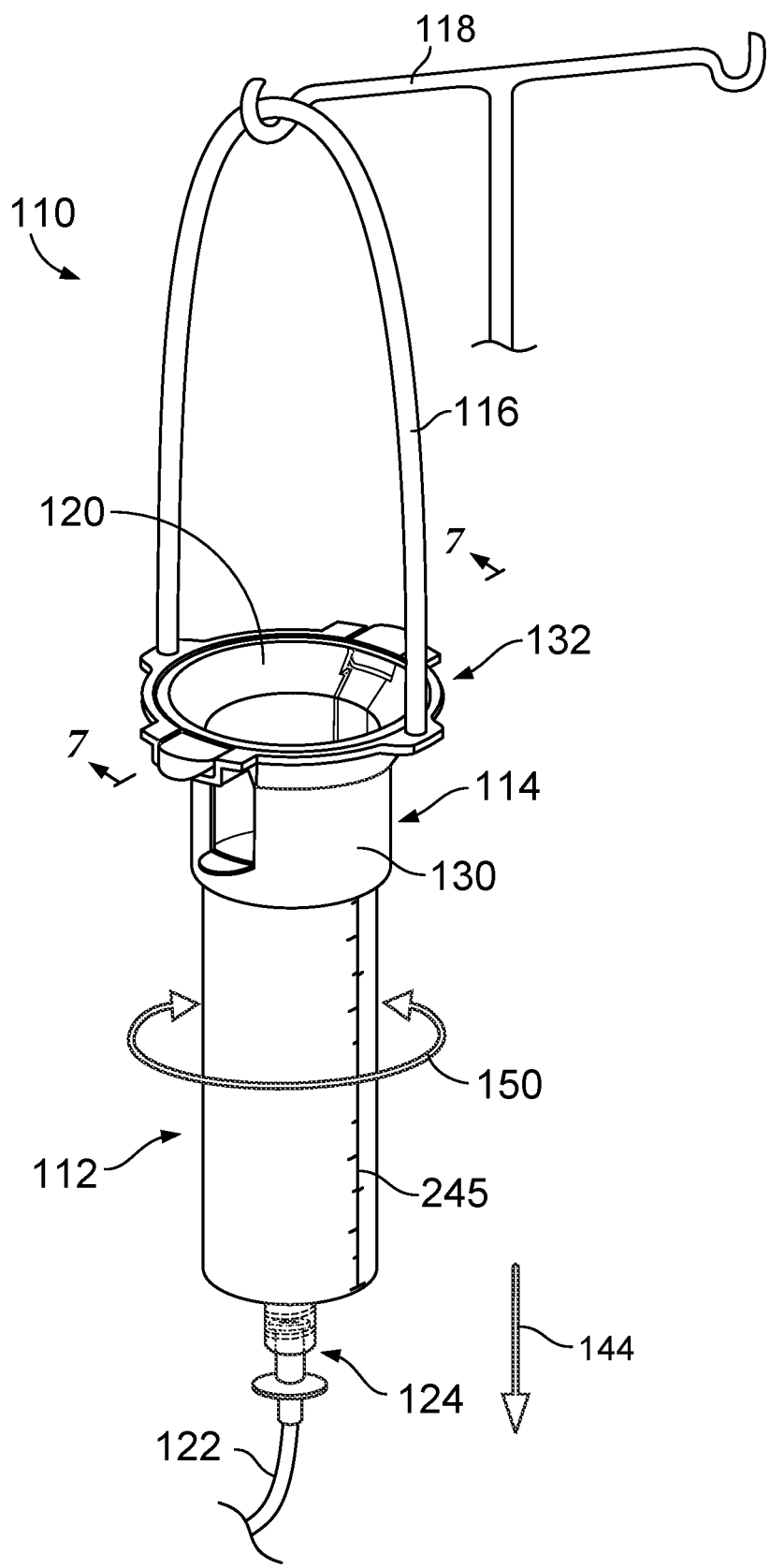
FIG. 5 is a perspective view of a formulated food solution delivery system including a holder having a handle hung on an intravenous pole and a syringe body received in the holder.

With reference to FIG. 5, a formulated food solution delivery system 110 is provided that includes a syringe body 112 for receiving a formulated food solution and a holder 114 having a handle 116 configured to be hung from a structure, such as an intravenous pole 118. The syringe body 112 may be configured to receive, for example, 160 cc of formulated food solution. The holder 114 includes a body 130 and a releasable connection 132 between the handle 116 and the body 130.

The syringe body 112 includes an upper opening 120 for receiving the formulated food solution and a tip 126 (see FIG. 6) configured to connected to a tube 122 via a connector 124. During use, the tube 122 is placed in communication with a patient's feeding tube and gravity draws the formulated food solution from within the syringe body 112, into the tube 122, into the patient's feeding tube, and into the patient's stomach. In one embodiment, the tip 126 includes a male thread. In another embodiment, the tip 126 may be connected to the tube 122 via an EnFit connection.

Figure 6:
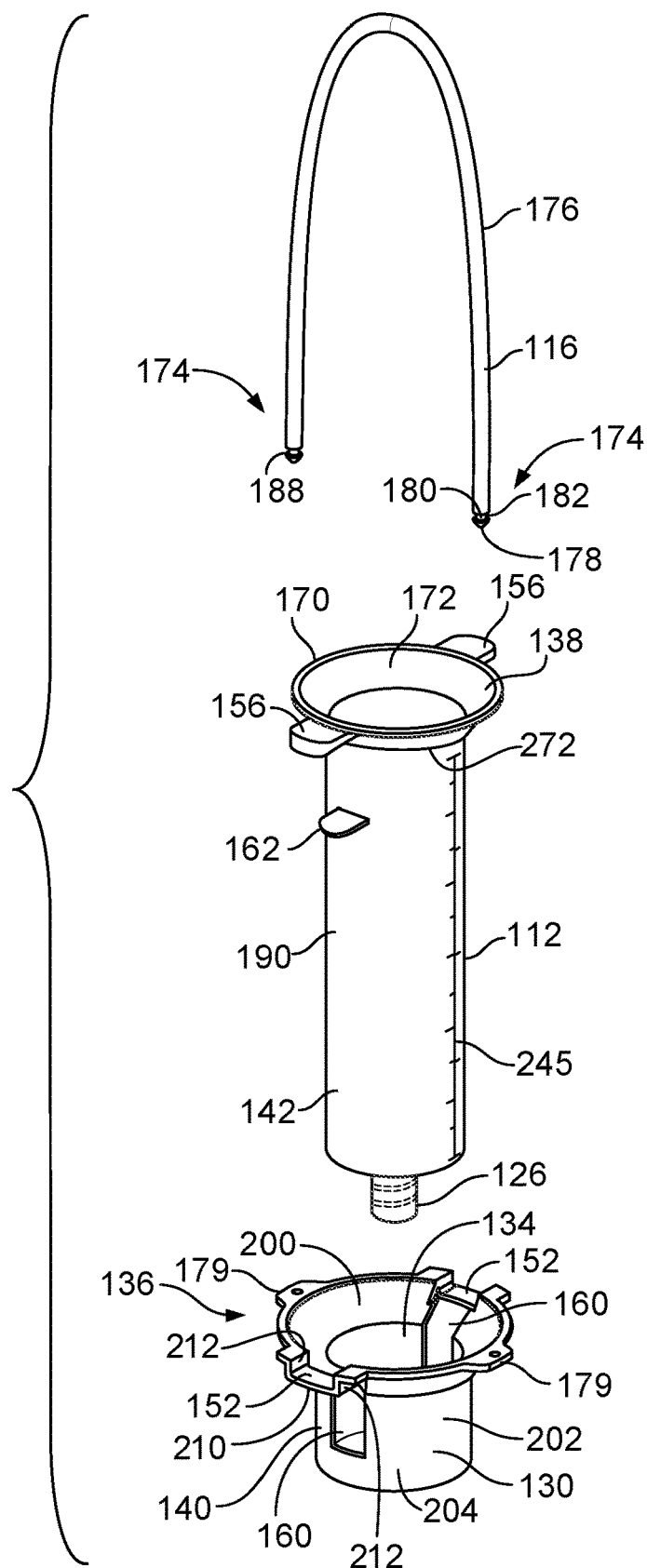
FIG. 6 is an exploded perspective view of the holder and syringe body of FIG. 5 showing the handle of the holder separated from a body of the holder.

Regarding FIGS. 5 and 6, the body 130 may have a generally tubular configuration with a central opening 134 that receives the syringe body 112. The body 130 includes an upper, collar-receiving portion 136 against which a collar 138 of the syringe body 112 seats. The body 130 further includes a lower, barrel-receiving portion 140 that extends around a barrel 142 of the syringe body 112. The upper, collar-receiving portion 136 resists movement of the syringe body 112 in direction 144 (see FIG. 5) and keeps the syringe body 112 securely held at the desired vertical position. One or more of the upper, collar-receiving portion 136 and the lower, barrel-receiving portion 140 includes at least one alignment portion that restricts rotary movement of the syringe body 112 in direction 150 within the body 130. In this manner, the body 130 provides a stable support for the syringe body 112 and resists any shifting of the syringe body 112, such as due to movement of the tube 122 due to patient movement.

In one embodiment, the at least one alignment portion includes one or more pockets 152 of the body 130 as shown in FIG. 6. The pockets 152 each receive a projection, such as an upper tab 156, of the syringe body 112. The at least one alignment portion may also include one or more openings 160 of the body 130. The openings 160 each receive a projection, such as a lower tab 162, of the syringe body 112. The collar 138 of the syringe body 112 includes a flange or rim 170, a frustoconical wall 172 extending radially inward from the rim 170, and the tabs 156 extending radially outwardly from the rim 170.

The handle 116 includes a pair of opposite end portions 174 and a loop portion 176 extending therebetween. Each end portion 174 includes a head portion 178, a neck portion 180, and a gap 182 extending around the neck portion 180. The upper, collar-receiving portion 136 of the body 130 of the holder 114 includes tabs 179 with openings 184 (see FIG. 8) that receive the head portions 178 of the handle 116. In one approach, the head portions 178 of the handle 116 each have a maximum diameter thereacross that is slightly larger than a diameter of the associated opening 184 of the tab 179.

To connect the handle end portion 174 to one of the tabs 179, the head portion 178 is advanced into the opening 184 of the tab 179 until the head portion 178 snaps below the tab 179. With the head portion 178 below the tab 179, the head portion 178 has an upper surface 188 that contacts a lower surface 181 (see FIG. 9) of the tab 179 and supports the body 130. The neck portion 180 extends through the opening 184 and has an outer diameter slightly smaller than the opening 184 to provide a snug fit of the neck portion 180 in the opening 184. The connection between the handle end portions 174 and the tabs 179 of the body 130 orients the handle end portions 174 so that the handle end portions 174 each extend generally normal to the associated tab 179. By generally normal, it is intended that there may be a slight curvature or angulation of the handle end portion 174 from normal as the handle end portion 174 extends away from the tab 179, such as an angulation of between 0.1 and 15 degrees from normal.

Regarding FIG. 6, the barrel 142 of the syringe body 112 includes an annular side wall 190 and the lower tabs 162 project radially outward from the side wall 190. In one embodiment, the upper tabs 156 and the lower tabs 162 are vertically aligned so that both the upper tabs 156 and lower tabs 162 advance into the openings 160 on the opposite sides of the body 130 as the syringe body 112 is positioned in the holder 114. In one embodiment, the upper, collar-receiving portion 136 of the holder 114 includes a frustoconical wall portion 200 that extends around and supports the collar 138 of the syringe body 112 once the syringe body 112 has been positioned in the opening 134 of the body 130. The body 130 also includes a sleeve 202 that extends around the barrel 142 of the syringe body 112. The inner diameter of the sleeve 202 is sized slightly larger than the outer diameter of the barrel 142 so that the barrel 142 is firmly received within the sleeve 202. In one approach, the sleeve 202 includes a collar portion 204 that extends completely around the barrel 142 without interruption to provide a stable connection between the body 130 of the holder 114 and the syringe body 112.

Figure 7:
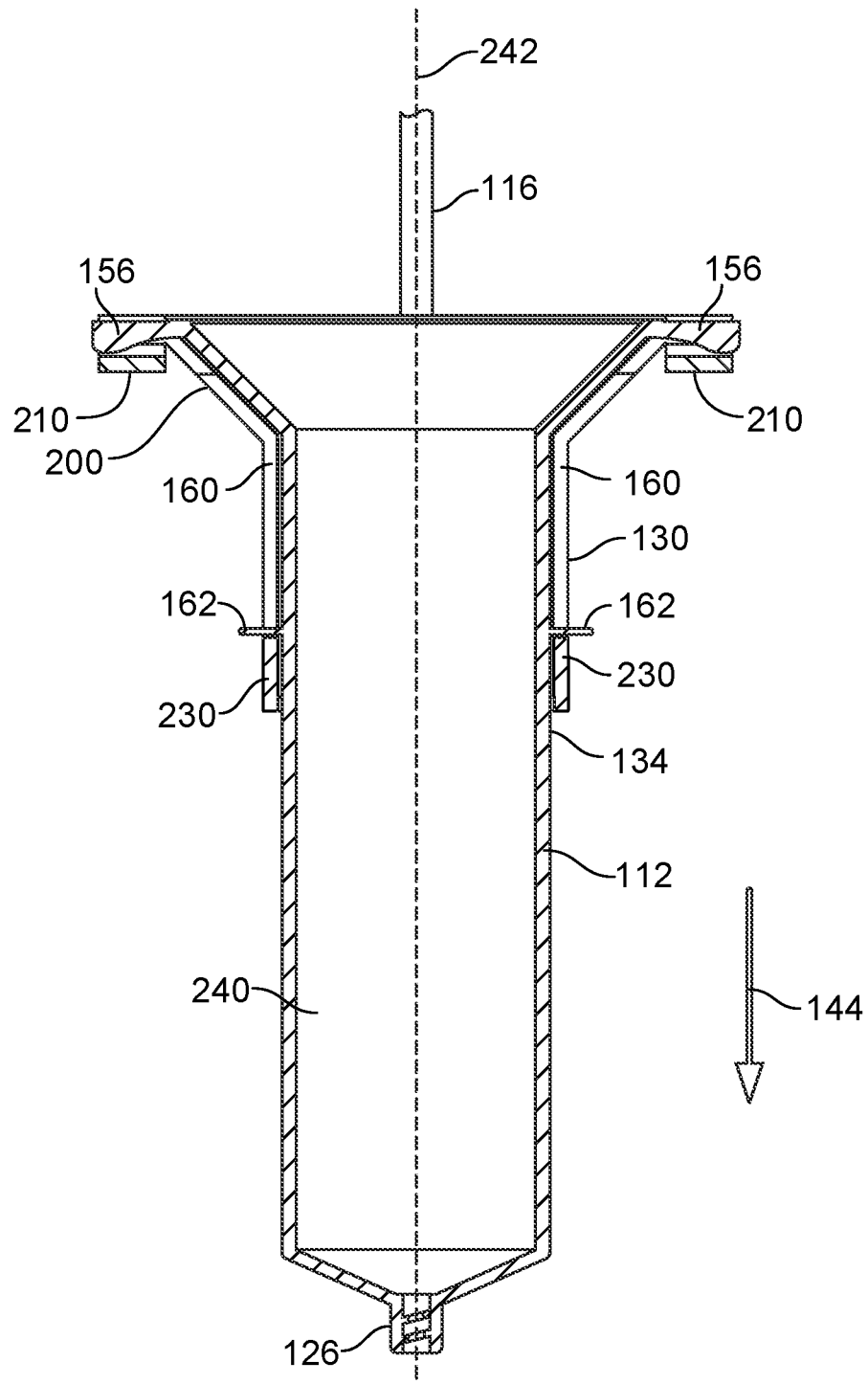
FIG. 7 is a cross-sectional view taken across line 7-7 in FIG. 5 showing lower tabs of the syringe body extending laterally outward through openings of the holder body and upper tabs of the syringe body received in pockets of the holder body.
Figure 9:
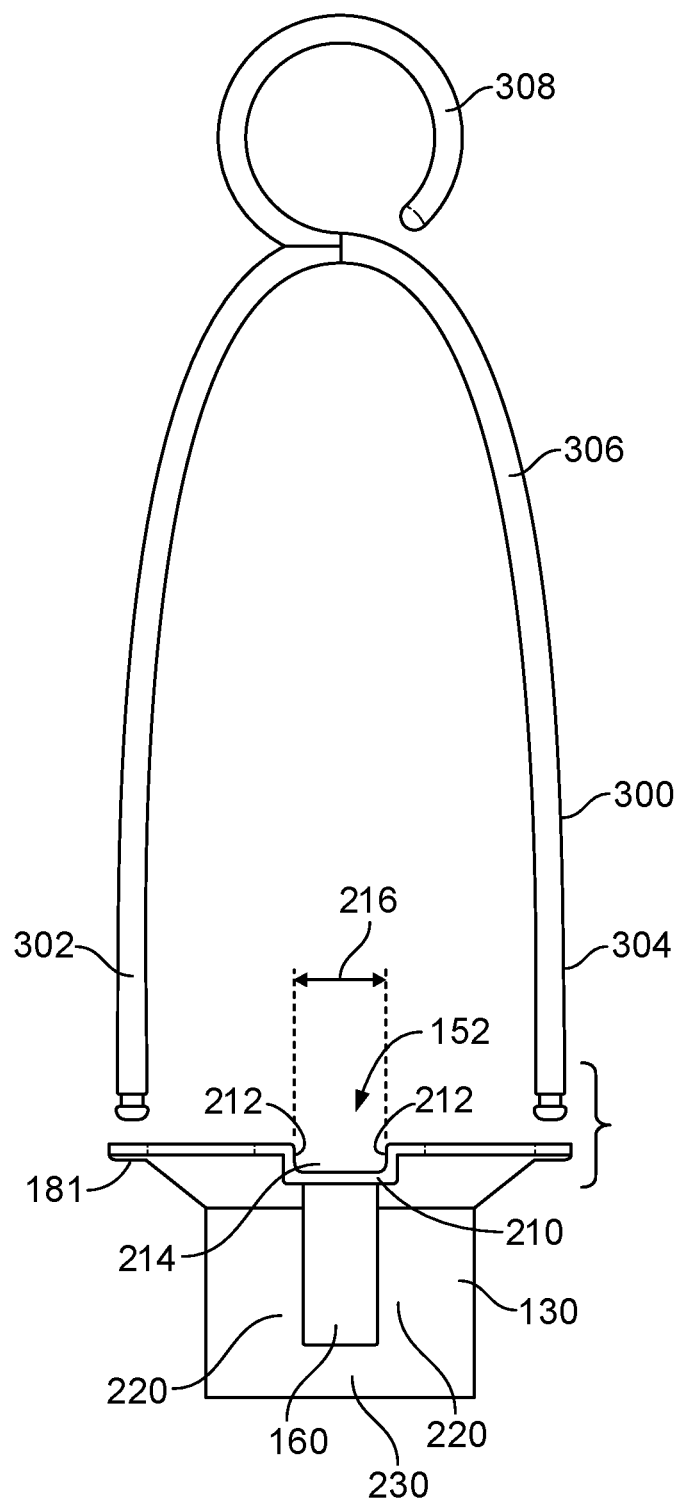
FIG. 9 is an elevational, exploded view of another holder with a handle that includes a hook.

With reference to FIGS. 4 and 7, each pocket 152 of the body 130 includes a floor 210 that extends below the associated upper tab 156 of the syringe body 112 and a pair of side walls 212 that extend upward along opposite sides of the upper tab 156. With reference to FIG. 9, the side walls 212 are separated by a gap 214 having a distance 216 sized to permit the upper tab 156 to be advanced downwardly into the gap 214 and seated against the floor 210. The sleeve 202 includes wall portions 220 on opposite sides of the opening 160. When one of the lower tabs 162 of the syringe body 112 is received in the opening 160, the lower tab 162 will contact or be adjacent to the wall portions 220. In this manner, contact between the lower tab 162 and one of the wall portions 220 resists turning of the syringe body 112 in direction 150 relative to the body 130.

Turning to FIGS. 7 and 9, the lower tabs 162 of the syringe body 112 may seat against bridge portions 230 of the body 130 that connect the wall portions 220. Further, the upper tabs 156 of the syringe body 112 seat against the floors 210 of the pockets 152 of the body 130. This engagement resists movement of the syringe body 112 in direction 144 (see FIG. 5) under the weight of the formulated food solution in an internal volume 240 of the syringe body 112. Regarding FIG. 7, the central opening 134 of the body 130 extends along a longitudinal axis 242 and the upper and lower tabs 156, 162 of the syringe body 112 extend laterally outward onto the floors 210 and the bridge portions 230 of the body 130.

In one embodiment, the body 130 has an axial length that is less than half of the axial length of the syringe body 112. This permits the tip 126 to be exposed for ready connection to the tube 122 as shown in FIGS. 5 and 6. This also permits viewing of a measurement indicium, such as calibrations 245, on the exterior of the barrel 142 of the syringe body 112. In this manner, a patient may readily visually confirm that the syringe body 112 has been filled with the desired volume of formulated food solution.

Figure 8:
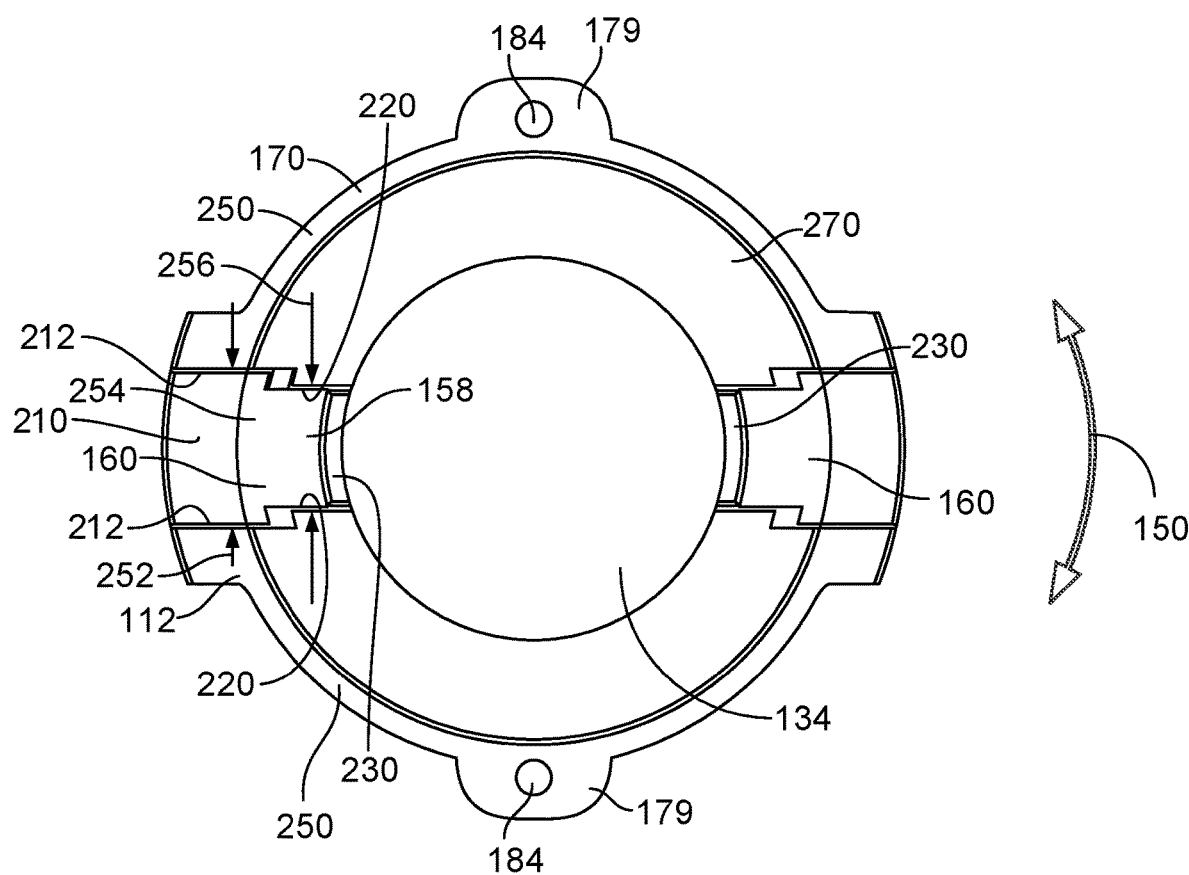
FIG. 8 is a top plan view of the holder body of FIG. 6 showing diametrically opposed openings of the holder body that receive the upper and lower tabs of the syringe body.

Regarding FIG. 8, the rim 170 of the syringe body 112 includes halves 250 separated by the openings 160. Each opening 160 includes a wide first portion 254 having a width 252 and a narrow second portion 258 having a width 256 that is less than the width 252. The different widths 252, 256 form a notched configuration of each of the openings 160. Further, the wide first portion 254 may accommodate a wider upper tab 156 while the narrow second portion 258 may more closely conform to the width of one of the narrower lower tabs 162. The body 130 of the holder 114 may thereby complement the protruding features of the syringe body 112.

As shown as in FIG. 8, the frustoconical wall 172 of the body 130 includes at least one upwardly facing upper surface 270. The upper surface 270 has a taper that matches the taper of a lower surface 272 of the collar 138 of the syringe body 112 (see FIG. 6). The nesting surfaces 270, 272 help provide a snug fit of the syringe body 112 in the holder 114.

With reference to FIG. 9, another handle 300 is provided that may be used to connect the body 130 to a support structure. The handle 300 includes end portions 302, 304 and a loop portion 306 extending therebetween. The handle 300 also includes a hook 308 that may be looped over a structure to assist in hanging the handle 300 from a support structure. The handles 116, 300 may be releasably connected to the body 130 to permit a user to select the handle 116, 300 for a particular application. The body 130 and one or more of the handles 116, 300 may be provided in a kit with the syringe body 112 and tube 122.

In one embodiment, the holder 114 is made of one or more plastic materials, such as polypropylene or acrylonitrile butadiene styrene (ABS), and may be manufactured using an injection molding process. For example, the body 130 may be made using a one-shot injection molding process. The body 130 and the handles 116, 300 may be made of different materials. For example, the body 130 may be made of a first polypropylene having a first shore durometer hardness and the handles 116, 300 may be made of a second polypropylene having a different, second shore durometer hardness.

In one approach, the system 110 is used to administer a formulated food solution by first positioning the syringe body 112 in the body 130 of the holder 114. Next, the handle 300 (for example) is attached to the body 130 and the tube 122 is connected to the syringe body tip 126. The tube 122 is connected to the patient's feeding tube. The holder 114 and syringe body 112 therein are then hung on a structure such as the intravenous pole 118 or a door. The interior volume 240 of the syringe body 112 is filled with the desired volume of the formulated food solution, which the patient can visually confirm using the exposed calibrations 245. Gravity draws the formulated food solution into the tube 122, into the patient's feeding tube, and into the patient's stomach.

Figure 10:
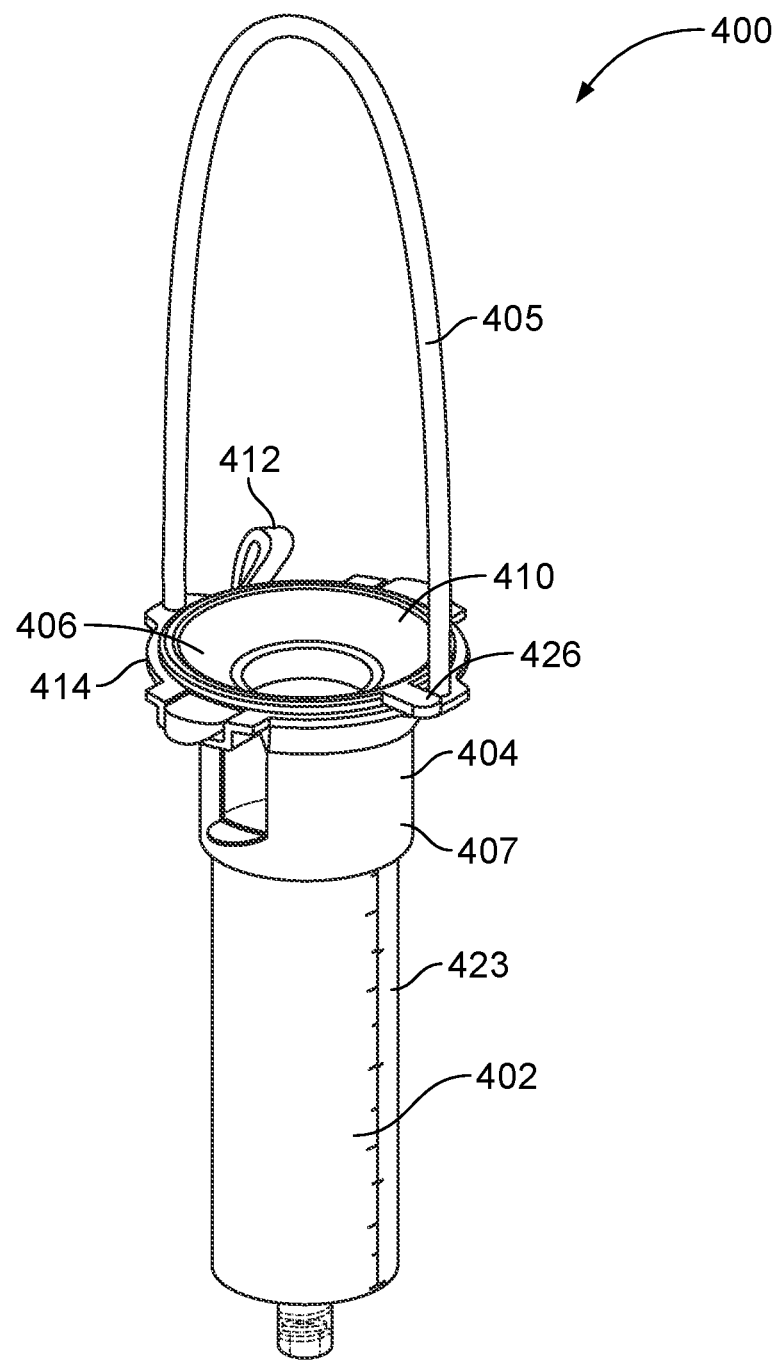
FIG. 10 is a perspective view of a formulated food solution delivery system including a holder, a syringe body received in the holder, and a cap of the holder in a closed position wherein the cap covers an opening of the syringe body.
Figure 11:
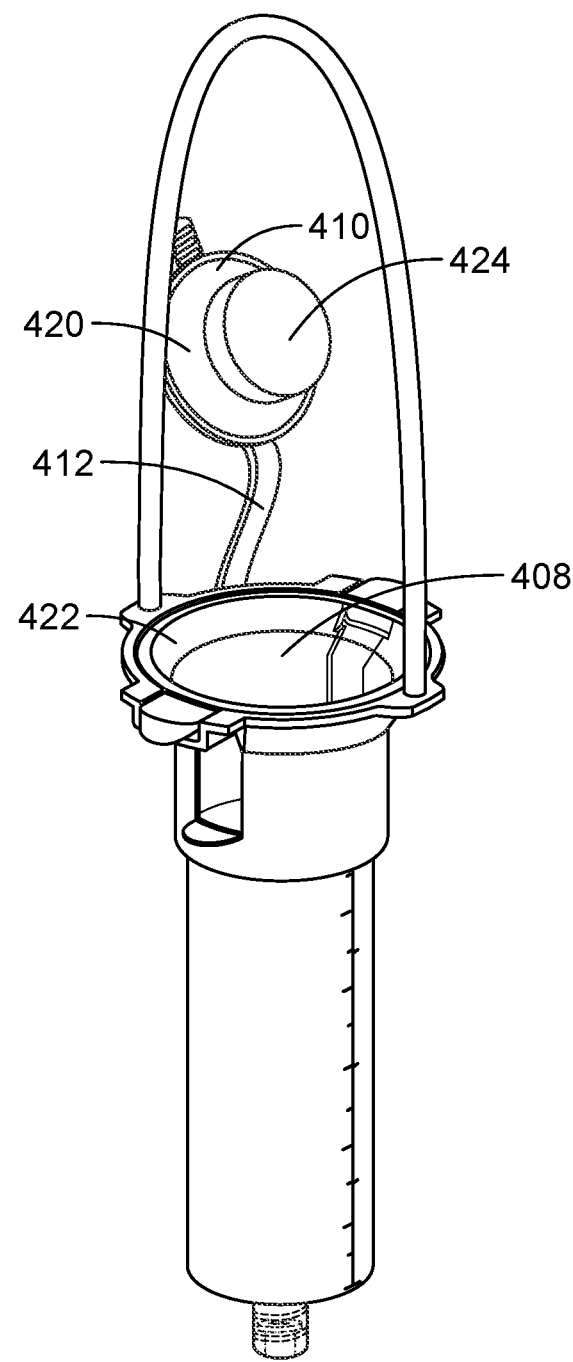
FIG. 11 is a perspective view similar to FIG. 10 showing the cap in an open position.

With reference to FIG. 10, a formulated food solution delivery system 400 is provided that is similar in many respects to the system 110 discussed above such that differences between the systems 110, 400 will be highlighted. The formulated food solution delivery system 400 includes a syringe body 402 and a holder 404. The holder 404 includes a handle 405 and a lid 406. The syringe body 402 includes an opening 408 (see FIG. 11) for receiving formulated food solution and the lid 406 is movable between a closed position (see FIG. 10) wherein the lid 406 covers the opening 408 and an open position (see FIG. 11) wherein the opening 408 is uncovered. By covering the opening 408, the lid 406 resists egress of formulated food solution outward through the opening 408 from within the syringe body 402. This reduces the risk of a user spilling the formulated food solution such as if the user inadvertently bumps the formulated food solution delivery system 400 during a feeding.

The lid 406 may be made of a flexible material, such as a polypropylene, and may be made of the same material as the handle 405. The lid 406 includes a cover portion 410 connected to a flange 414 of the holder 404 by a connector such as a tether 412. In one embodiment, the lid 406 has a unitary, one-piece construction including the cover portion 410 and the tether 412. The tether 412 is elongate and includes a barb configured to fit in an opening of a flange 414 of a body 407 of the holder 404.

The cover portion 410 has a frustoconical portion 420 that seats against a frustoconical portion 422 of the syringe body 402. The cover portion 410 further includes a plug portion 424 configured to occlude the opening 408 of the syringe body 402. For example, the syringe body 402 may have a cylindrical wall 423 with an inner diameter and the plug portion 424 of the lid 406 has an outer diameter larger than the inner diameter. This causes the plug portion 424 to form a press fit with the cylindrical wall 423 when the lid 406 is in the closed position. The press fit between the lid 406 and the syringe body 402 provides a seal that resists egress of formulated food solution outward through the opening 408 of the syringe body 402. To open the lid 406, the user pulls upward on a tab 426 of the lid 406 to disengage the plug portion 424 of the lid 406 from within the opening 408 of the syringe body 402.

Figure 12:
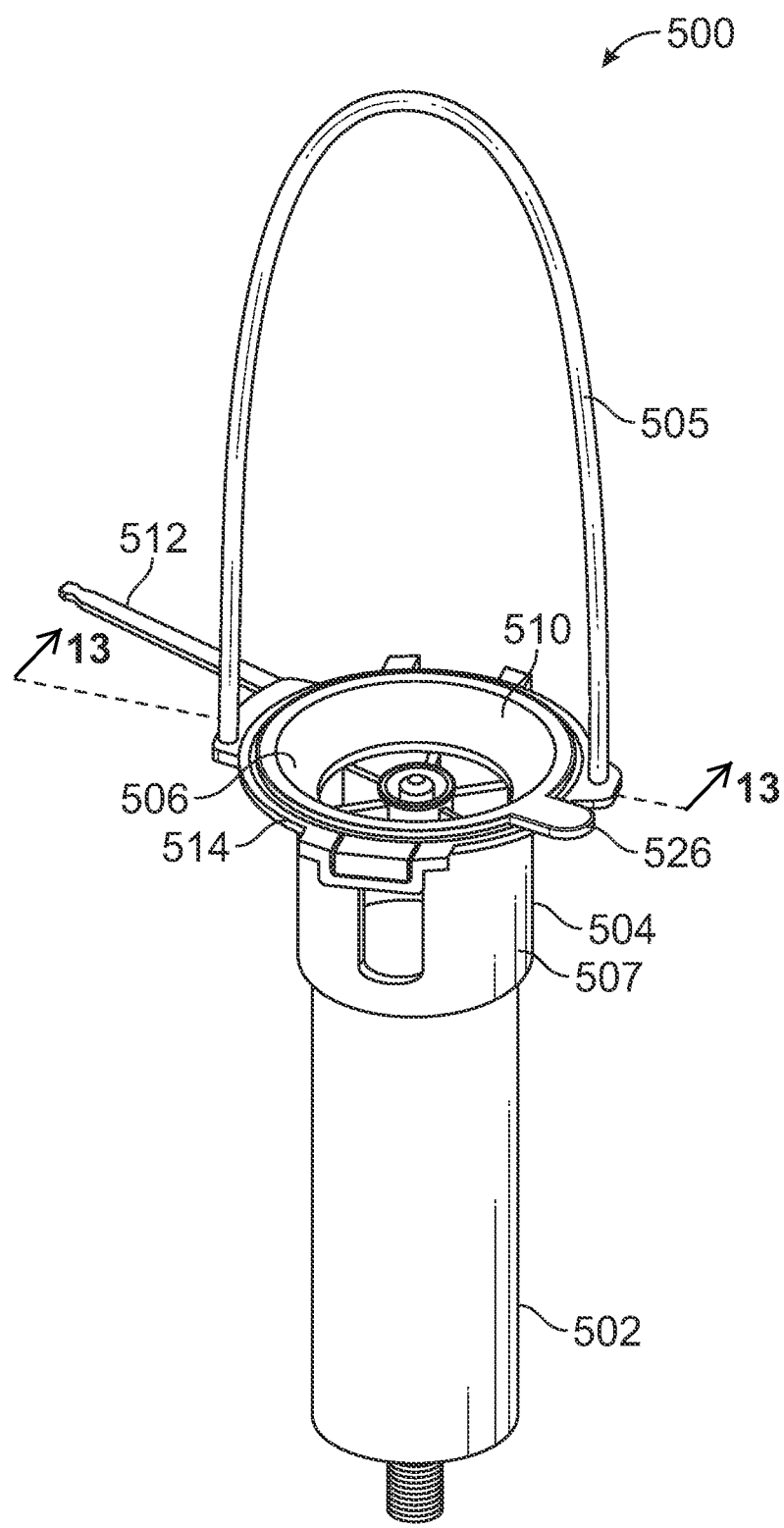
FIG. 12 is a perspective view of a formulated food solution delivery system including a lid having vented apertures.
Figure 13:
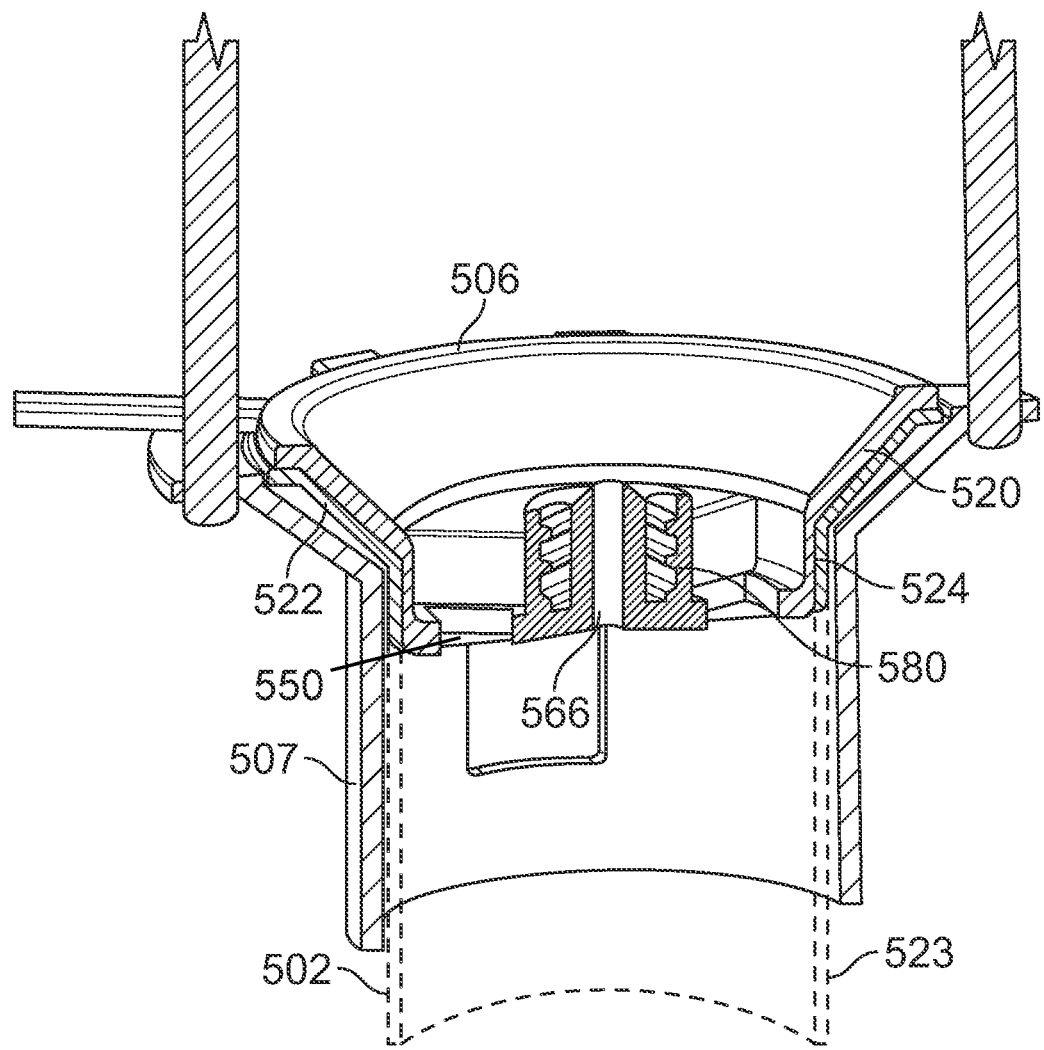
FIG. 13 is a cross-sectional view taken across line 13-13 in FIG. 12 showing the vented apertures.

With reference to FIGS. 12 and 13, a formulated food solution delivery system 500 is provided that is similar in many respects to the system 110 discussed above. The formulated food solution delivery system 500 includes a syringe body 502 and a holder 504. The holder 504 includes a handle 505 and a lid 506. The syringe body 502 includes an opening (similar to opening 120 of FIG. 5) for receiving formulated food solution and the lid 506 is movable between a closed position wherein the lid 506 covers the opening and an open position wherein the opening is uncovered. By covering the opening, the lid 506 resists egress of formulated food solution outward through the opening from within the syringe body 502. This reduces the risk of a user spilling the formulated food solution such as if the user inadvertently bumps the formulated food solution delivery system 500 during a feeding.

The lid 506 may be made of a flexible material, such as a polypropylene, and may be made of the same material as the handle 505. The lid 506 includes a cover portion 510 connected to a flange 514 of the holder 504 by a connector such as a tether 512. In one embodiment, the lid 506 has a unitary, one-piece construction including the cover portion 510 and the tether 512. The tether 512 is elongate and includes a barb configured to fit in an opening of a flange 514 of a body 507 of the holder 504, as described and depicted with regard to FIGS. 10 and 11. The body 507 may generally correspond to the body 130 discussed with respect to FIG. 5.

The cover portion 510 has a frustoconical portion 520 that seats against a frustoconical portion 522 of the body 507 of the syringe body 502. The cover portion 510 further includes a plug portion 524 configured to occlude the opening of the syringe body 502. For example, the syringe body 502 may have a cylindrical wall 523 with an inner diameter and the plug portion 524 of the lid 506 has an outer diameter larger than the inner diameter. This causes the plug portion 524 to form a press fit with the cylindrical wall 523 when the lid 506 is in the closed position. The press fit between the lid 506 and the syringe body 502 provides a seal that resists egress of formulated food solution outward through the opening of the syringe body 502. To open the lid 506, the user pulls upward on a tab 526 of the lid 506 to disengage the plug portion 524 of the lid 506 from within the opening of the syringe body 502.

Figure 14:
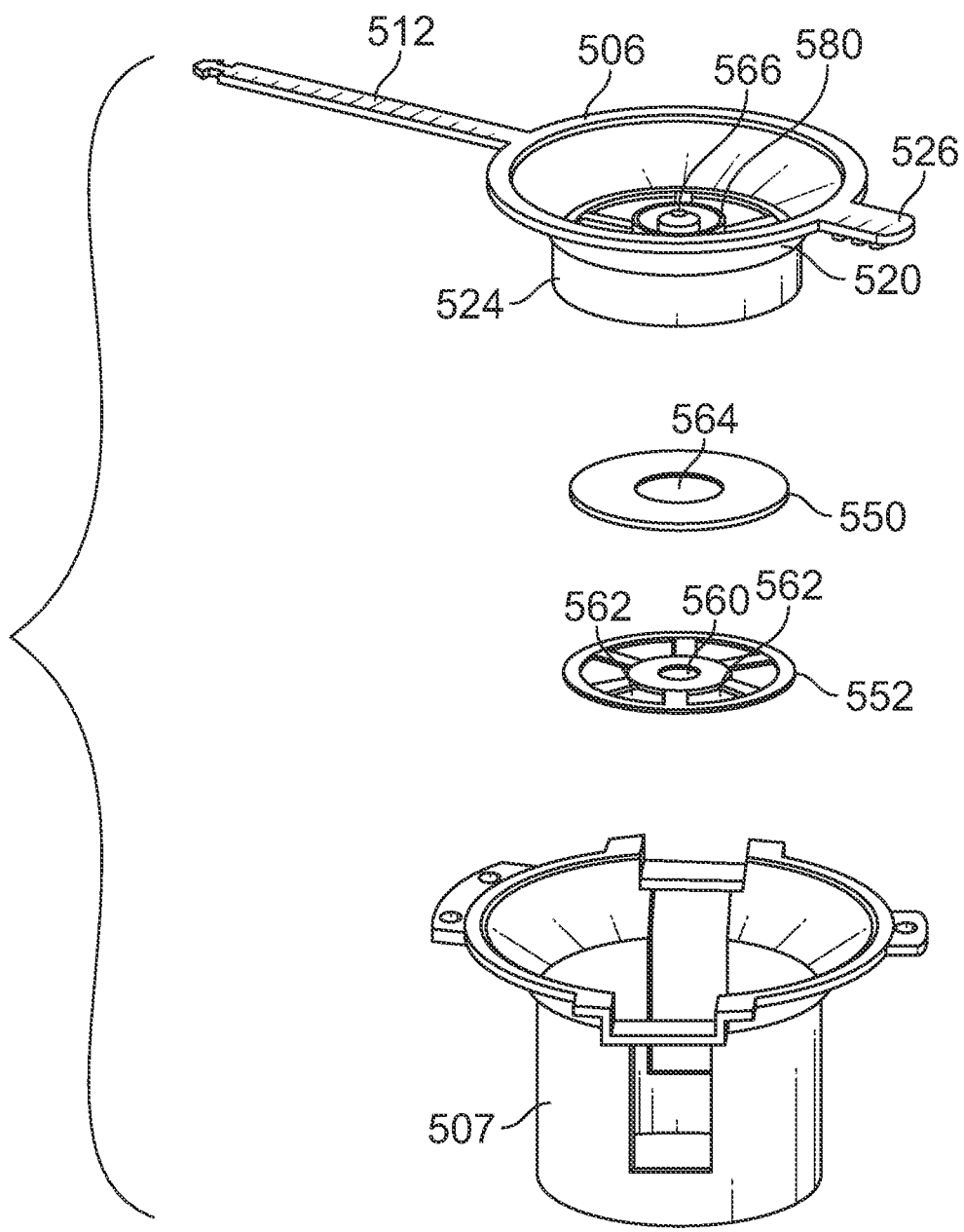
FIG. 14 is an exploded view of the lid, membrane, plate, and holder.

Referring to FIG. 14, the formulated food solution delivery system 500 may include a membrane 550 and a plate 552 that is configured to secure the membrane 550 to the lid 506. The membrane 550 may be in the form of any one, or combination of, the membranes previously discussed with respect to FIGS. 1-4. The membrane 500 may be in the form of an annular disc having a through-hole 564.

The plate 552 may include one or more vent apertures. For example, a central aperture 560 may be axially aligned with the through-hole 564 of the membrane 550 and a through-hole 566 of the lid 506. One or more outer apertures 562 may be spaced radially outwardly from the central aperture 560, and may be angularly spaced about a central axis of the central aperture 560. In the example shown, six outer apertures 562 are spaced about the central aperture 560. The outer apertures 562 may be formed by ribs or walls that extend radially in a direction away from the central aperture 560.

The plate 552 may be secured to the lid 506 using bonding techniques including solvents, UV cured adhesives; welding techniques including ultrasonic, thermal or spin techniques; or snap fits and/or other mechanical attachment devices. In still another approach, the plate 552 may be omitted, and the membrane 550 may be secured to the lid 506 through any suitable approach including the aforementioned approaches. Furthermore, although depicted as being secured to a lower surface of the lid 506, it is expressly contemplated that one or both of the membrane 550 and plate 552 may be secured to an upper surface of the lid 506 (e.g., adjacent and around the connection interface 580 described in greater detail below).

Figure 15:
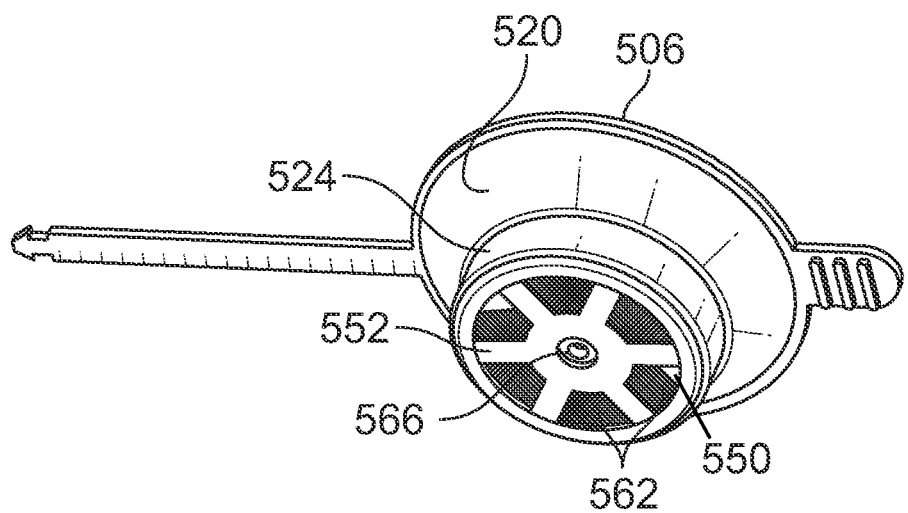
FIG. 15 is a bottom perspective view of the lid.
Figure 16:
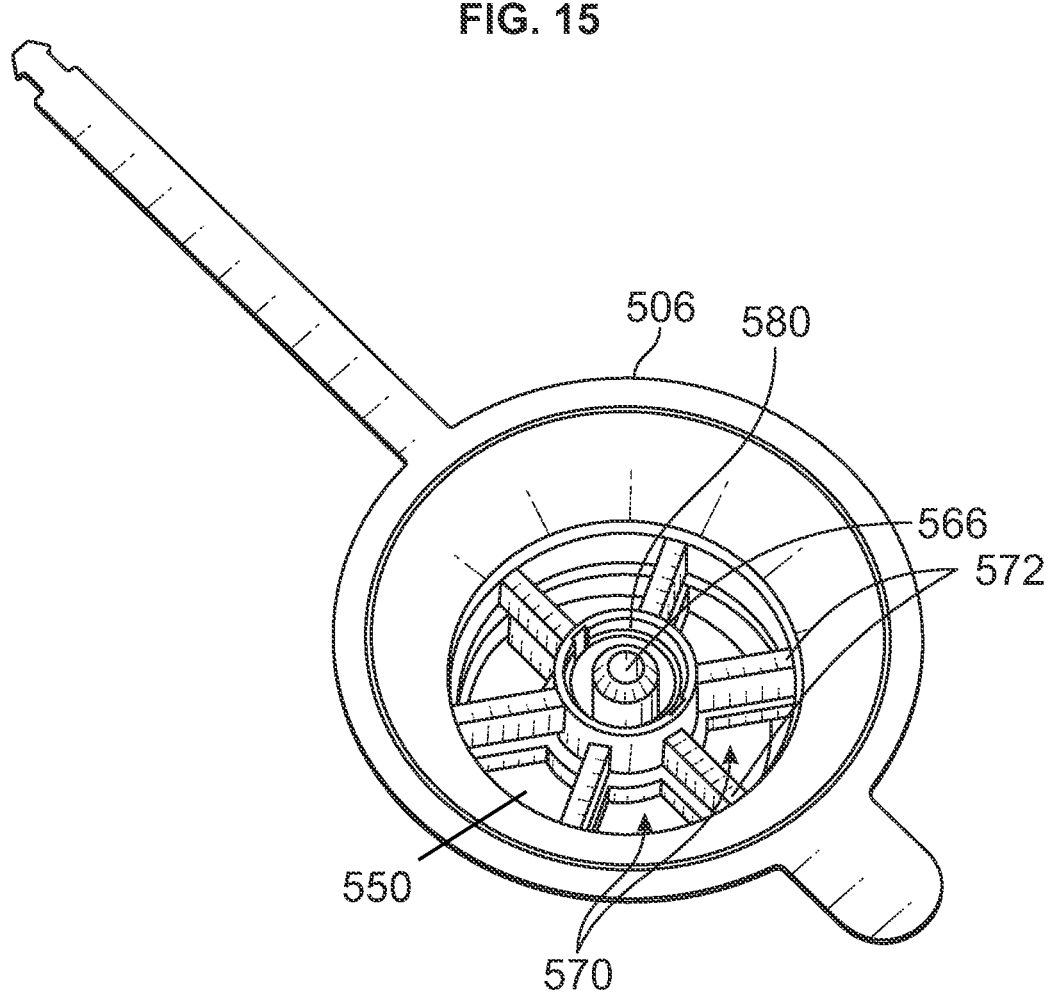
FIG. 16 is a top perspective view of the lid.

Referring to FIGS. 15 and 16, the central aperture 560 may be aligned (e.g., vertically aligned) with the through-hole 566 of the lid 506. Furthermore, the outer apertures 562 may be aligned (e.g., vertically aligned) with outer apertures 570 of the lid 506. The outer apertures 570 of the lid 506 may be formed by one or more ribs 572. The ribs 572 may extend from the plug portion 524 of the lid 506 to a connection interface 580 that is disposed about the through-hole 566 of the lid 506. The connection interface 580 may be in the form of an EnFit connection. Other connection interfaces (e.g., male thread) are expressly contemplated. In this way, conduit such as a flexible tube may be secured to the lid 506 in a fluid-tight manner. The connection interface 580 may permit fluid from a fluid source to communicate with the chamber formed by the syringe body 502 through the through-hole 566 of the lid 506, through the through-hole 564 of the membrane 550, and through the central aperture 560 of the plate 552.

Figure 17:
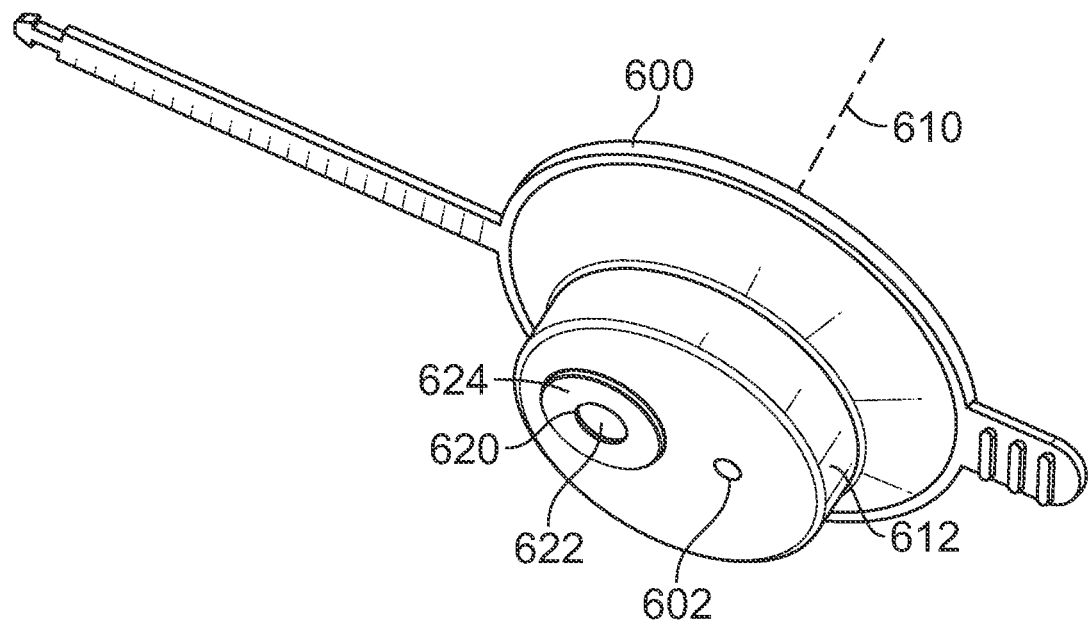
FIG. 17 is a bottom perspective view of an alternative lid.
Figure 18:
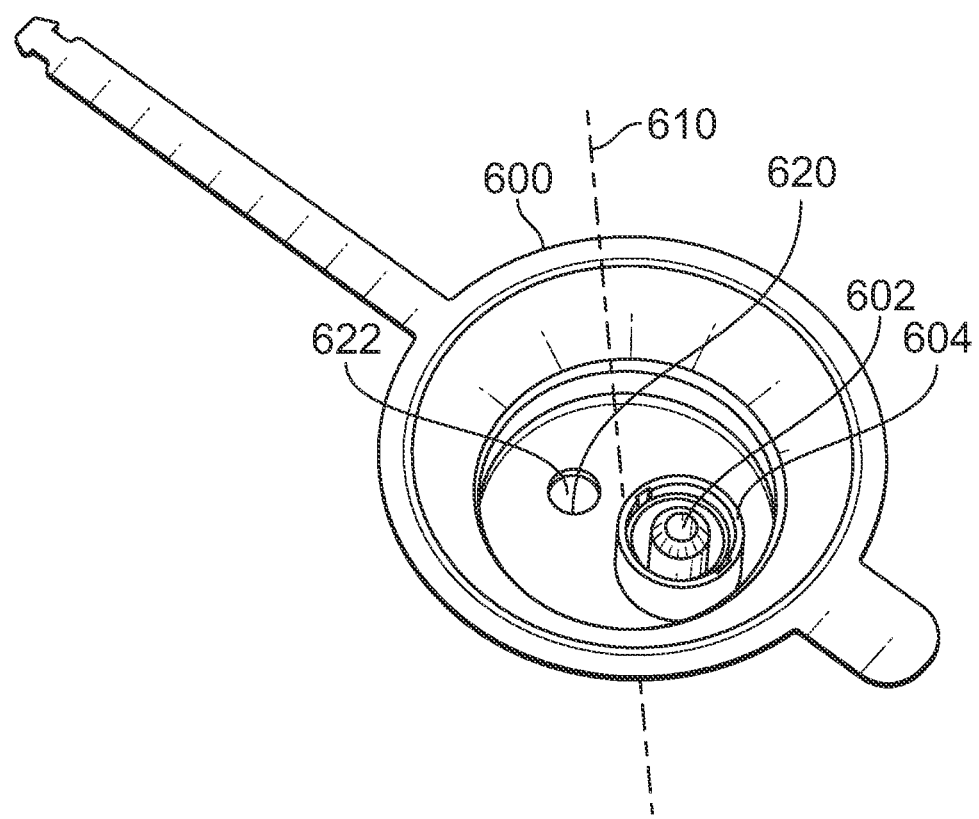
FIG. 18 is a top perspective view of the alternative lid.

Referring to FIGS. 17 and 18, another lid 600 is shown. The lid 600 may share many of the same features and characteristics as those described with respect to lid 506. Lid 600 includes a through-hole 602, and a connection interface 604 that is aligned with and extends about the through-hole 602. The through-hole 602 may be offset from a central axis of the lid 600 (e.g., offset from a central axis 610 of the plug portion 612 of the lid 600).

The lid 600 may further include vent aperture 620, and a membrane 622 that extends across the vent aperture 620. The vent aperture 620 may be offset from a central axis of the lid 600 (e.g., offset from a central axis 610 of the plug portion 612 of the lid 600). The membrane 622 may have a reduced size as compared to membrane 550 previously discussed. A plate 624 may be provided to secured the membrane 622 to the lid 600.

Although depicted as being secured to a lower surface of the lid 600, it is expressly contemplated that one or both of the membrane 622 and plate 624 may be secured to an upper surface of the lid 600 (e.g., adjacent to the connection interface 604).

It is expressly contemplated that the various features described herein (e.g., with respect to system 10, formulated food solution delivery system 110, formulated food solution delivery system 400, formulated food solution delivery system 500, etc.) may be used interchangeably. As such, syringes 11, 11' having membranes 28, 28' may also be provided with the various holders, lids, etc. discussed herein.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A lid assembly for a syringe body of a formulated food solution delivery system, the assembly comprising:
   a lid movable between a closed position wherein the lid covers an opening of the syringe body and an open position wherein the lid is spaced from the opening of the syringe body, the lid including a through-hole for permitting fluidic communication with a chamber of the syringe body;
   a connector interface of the lid being disposed about the through-hole;
   a gas-permeable membrane secured to the lid at a region offset from the through-hole, the gas-permeable membrane being resistant to liquid passage; and
   a plate secured to the lid, the gas-permeable membrane being disposed between at least a portion of the plate and the lid;
   wherein the lid defines a lid vent, wherein the plate defines a plate vent at least partially aligned with the lid vent to define a partially aligned portion, and wherein the gas-permeable membrane extends across at least a portion of the partially aligned portion.

2. The lid assembly of claim 1 wherein the through-hole is coaxial with a central axis of the lid.

3. The lid assembly of claim 1 wherein the through-hole is provided at a region that is spaced apart from a central axis of the lid.

4. The lid assembly of claim 1 wherein the lid defines a plurality of outer vent holes angularly spaced about the through-hole.

5. The lid assembly of claim 4 wherein the gas-permeable membrane is disposed along the lid so as to extend across the plurality of outer vent holes and to not extend across at least a portion of the through-hole.

6. The lid assembly of claim 1 wherein the lid includes a plurality of ribs that at least partially define the lid vent.

7. The lid assembly of claim 6 wherein the plurality of ribs extend radially outwardly from the connector interface.

8. A lid assembly for a syringe body of a formulated food solution delivery system, the assembly comprising:
   a lid movable between a closed position wherein the lid covers an opening of the syringe body and an open position wherein the lid is spaced from the opening of the syringe body, the lid including a through-hole for permitting fluidic communication with a chamber of the syringe body;
   a connector interface of the lid being disposed about the through-hole;
   a gas-permeable membrane secured to the lid at a region offset from the through-hole, the gas-permeable membrane being resistant to liquid passage, wherein the membrane has a moisture vapor transmission rate value (MVTR) of greater than approximately 300 $g/m^2/day$;
   a plate secured to the lid, the gas-permeable membrane being disposed between at least a portion of the plate and the lid;
   wherein the lid defines a lid vent, wherein the plate defines a plate vent at least partially aligned with the lid vent to define a partially aligned portion, and wherein the gas-permeable membrane extends across at least a portion of the partially aligned portion.

9. The lid assembly of claim 8 wherein the through-hole is coaxial with a central axis of the lid.

10. The lid assembly of claim 8 wherein the through-hole is provided at a region that is spaced apart from a central axis of the lid.

11. The lid assembly of claim 8 wherein the lid defines a plurality of outer vent holes angularly spaced about the through-hole.

12. The lid assembly of claim 11 wherein the gas-permeable membrane is disposed along the lid so as to extend across the plurality of outer vent holes and to not extend across at least a portion of the through-hole.

13. The lid assembly of claim 8, wherein the lid includes a plurality of ribs that at least partially define the lid vent.

14. The lid assembly of claim 13 wherein the plurality of ribs extend radially outwardly from the connector interface.

* * * * *